US00PP34320P2

(12) United States Plant Patent
Escobedo et al.

(10) Patent No.: US PP34,320 P2
(45) Date of Patent: Jun. 14, 2022

(54) BLACKBERRY PLANT NAMED 'DRISBLACKTWENTYSIX'

(50) Latin Name: ***Rubus* L. subgenus *Rubus*.**
Varietal Denomination: DrisBlackTwentySix

(71) Applicant: Driscoll's, Inc., Watsonville, CA (US)

(72) Inventors: Missael Bonifacio Romero Escobedo, Watsonville, CA (US); Gavin R. Sills, Watsonville, CA (US); Mark F. Crusha, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/338,323

(22) Filed: Jun. 3, 2021

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear et al. |
| PP13,758 | P3 | 5/2003 | Fear et al. |
| PP13,759 | P3 | 5/2003 | Fear et al. |
| PP14,682 | P3 | 4/2004 | Fear et al. |
| PP14,765 | P2 | 5/2004 | Cook et al. |
| PP14,780 | P2 | 5/2004 | Cook et al. |
| PP15,058 | P2 | 8/2004 | Cook et al. |
| PP17,162 | P3 | 10/2006 | Moore et al. |
| PP17,983 | P2 | 9/2007 | Cabrera |
| PP22,002 | P2 | 7/2011 | Pabon et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Rodriguez et al. |
| PP24,701 | P3 | 7/2014 | Rodriguez et al. |
| PP24,878 | P2 | 9/2014 | Alcazar et al. |
| PP25,502 | P3 | 5/2015 | Pabon et al. |
| PP26,501 | P3 | 3/2016 | Pabon et al. |
| PP26,611 | P3 | 4/2016 | Pabon et al. |
| PP26,774 | P3 | 5/2016 | Pabon et al. |
| PP27,129 | P2 | 9/2016 | Sills et al. |
| PP27,130 | P2 | 9/2016 | Sills et al. |
| PP27,146 | P2 | 9/2016 | Sills et al. |
| PP27,681 | P3 | 2/2017 | Sills et al. |
| PP27,746 | P3 | 3/2017 | Sills et al. |
| PP28,548 | P2 | 10/2017 | Sills et al. |
| PP31,110 | P2 | 11/2019 | Sills et al. |
| PP31,291 | P2 | 12/2019 | Sills et al. |
| PP31,825 | P2 | 6/2020 | Sills et al. |
| PP31,826 | P2 | 6/2020 | Sills et al. |
| PP32,268 | P2 | 10/2020 | Sills et al. |
| PP33,067 | P2 | 5/2021 | Sills et al. |
| PP33,068 | P2 | 5/2021 | Sills et al. |
| PP33,088 | P2 | 5/2021 | Sills et al. |

OTHER PUBLICATIONS

Voss, Donald H., "The Royal Horticultural Society Colour Chart 2001," Journal American Rhododendron Society, vol. 56, No. 1, 2002, 3 pages.

Williams, et al., "DNA polymorphisms amplified by arbitrary primers are useful as genetic markers," Nucleic Acids Research, vol. 18, No. 22, 1990, pp. 6531-6535.

*Primary Examiner* — Susan McCormick Ewoldt
(74) *Attorney, Agent, or Firm* — Morrison & Foerster LLP

(57) ABSTRACT

A new and distinct variety of blackberry plant named 'DrisBlackTwentySix', particularly selected for its yield, fruit size, and fruit flavor, is disclosed.

4 Drawing Sheets

Botanical classification: *Rubus* L. subgenus *Rubus*.

Varietal denomination: The varietal denomination of the claimed variety of blackberry plant is 'DrisBlackTwentySix'.

BACKGROUND OF THE INVENTION

Blackberry is the common name for a multitude of plant species bearing dark purple to black aggregate fruit in the genus *Rubus* of the family Rosaceae. Most blackberries are within the subgenus *Rubus*.

Native chiefly to the northern temperate regions, blackberries are now being cultivated as a valuable fruit crop in many areas of the world, particularly in Europe, North America and Central America, Recognized for their high contents of antioxidants, dietary fiber, vitamin C, and vitamin K. Blackberry fruit are typically consumed as fresh fruit, individually quick frozen fruit, or in prepared foods, such as purées, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi' (also spelled as 'Tupy'). In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of three to six meters in a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed that are capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackTwentySix'.

Blackberry plant variety 'DrisBlackTwentySix' was selected in Ciudad Guzmán, Mexico in January of 2016 and originated from a cross between the female parent proprietary blackberry plant 'BR382.2' (unpatented) and the male parent proprietary blackberry plant 'BR502.2' (unpatented). The original seedling of the new variety was first asexually propagated via root cuttings in Ciudad Guzmán, Mexico in January of 2016.

'DrisBlackTwentySix' was subsequently asexually propagated via root cuttings, and has undergone testing in Ciudad Guzmán, Mexico from 2015 to 2021 (six years)(variety was under evaluation before being selected as a candidate variety in 2016). The present variety has been found to be stable and reproduce true to type through successive asexual propagations via root cuttings and tissue culture.

'DrisBlackTwentySix' was particularly selected for its yield, fruit size, and fruit flavor.

BRIEF DESCRIPTION OF THE DRAWINGS

This new blackberry plant is illustrated by the accompanying photographs. The colors shown are as true as can be reasonably obtained by conventional photographic procedures. The photographs are of plants that are three years old.

DETAILED BOTANICAL DESCRIPTION

Figure 1:
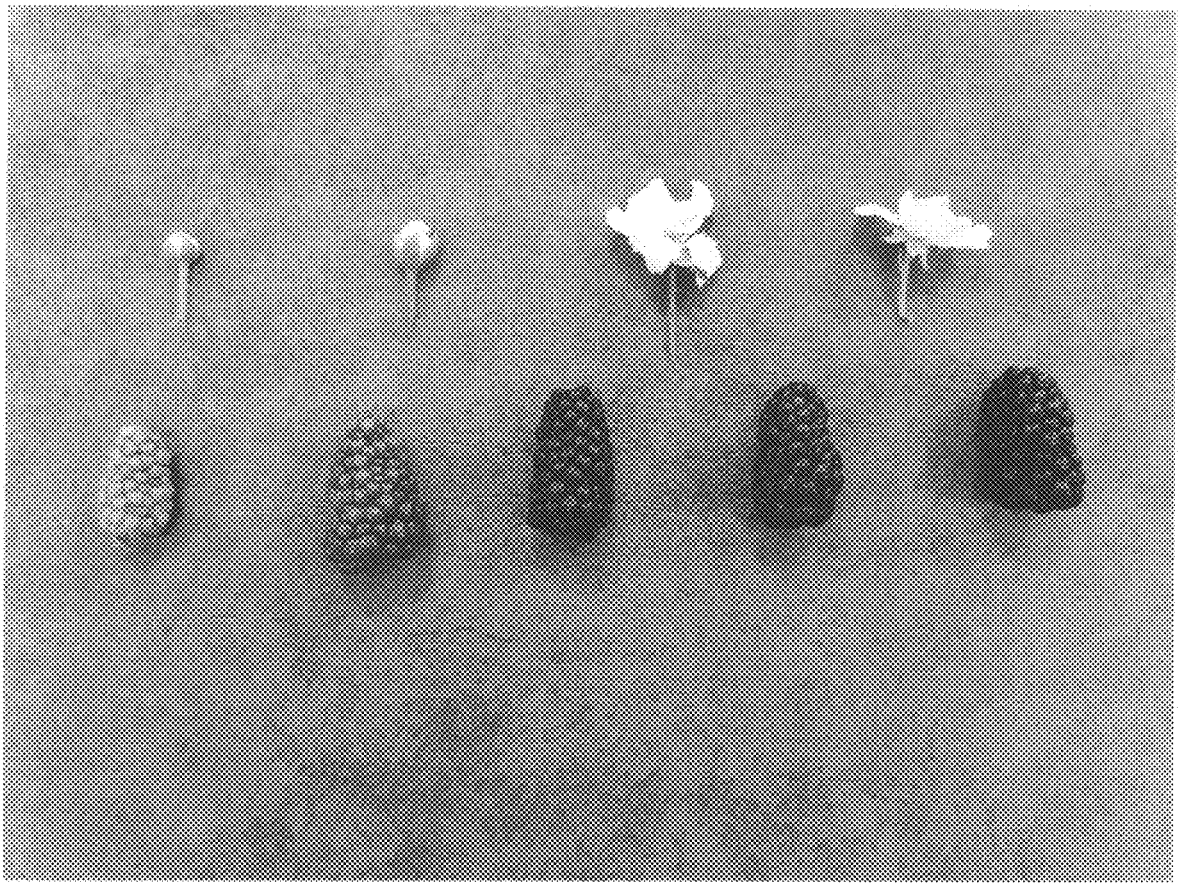
FIG. 1 illustrates flowers (upper row) and fruit (lower row) of variety 'DrisBlackTwentySix' at various stages of development.
Figure 2:
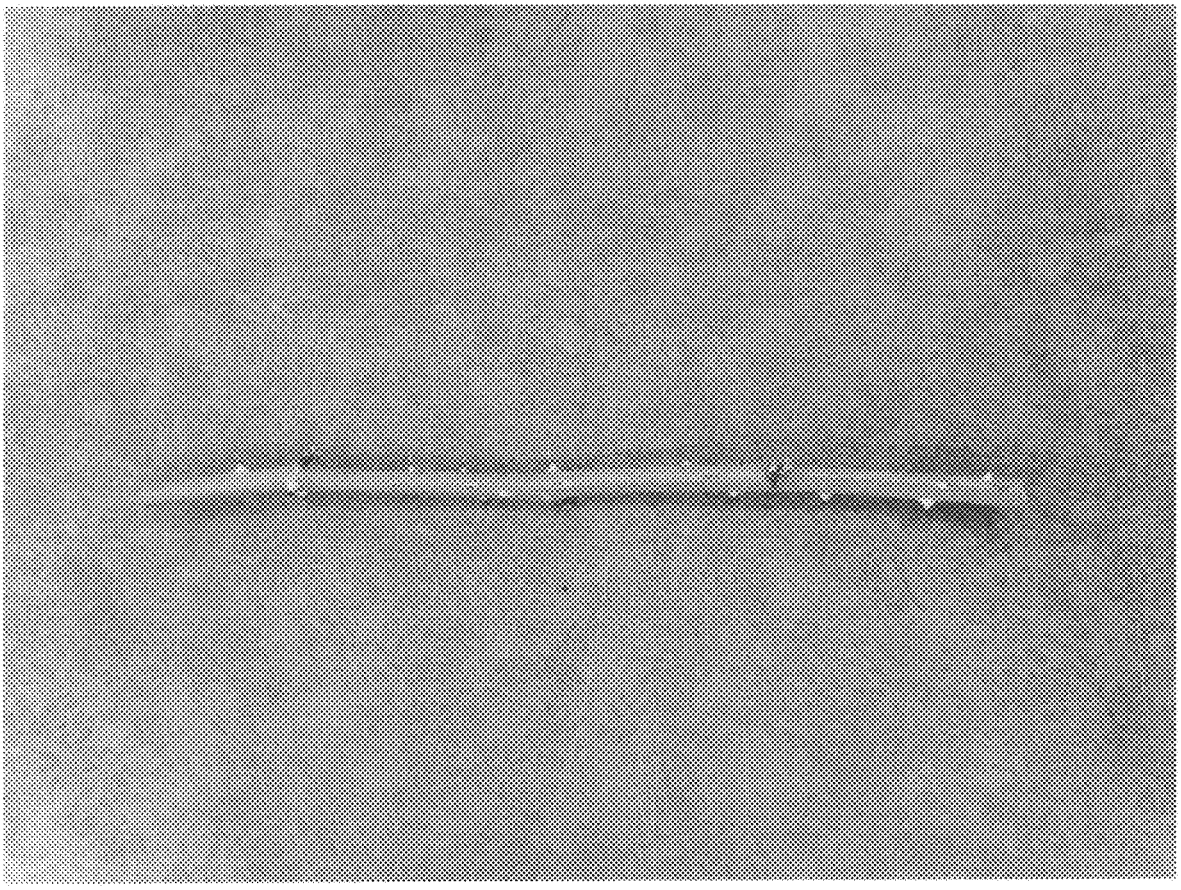
FIG. 2 illustrates the central third section of a cane of variety 'DrisBlackTwentySix'.
Figure 3:
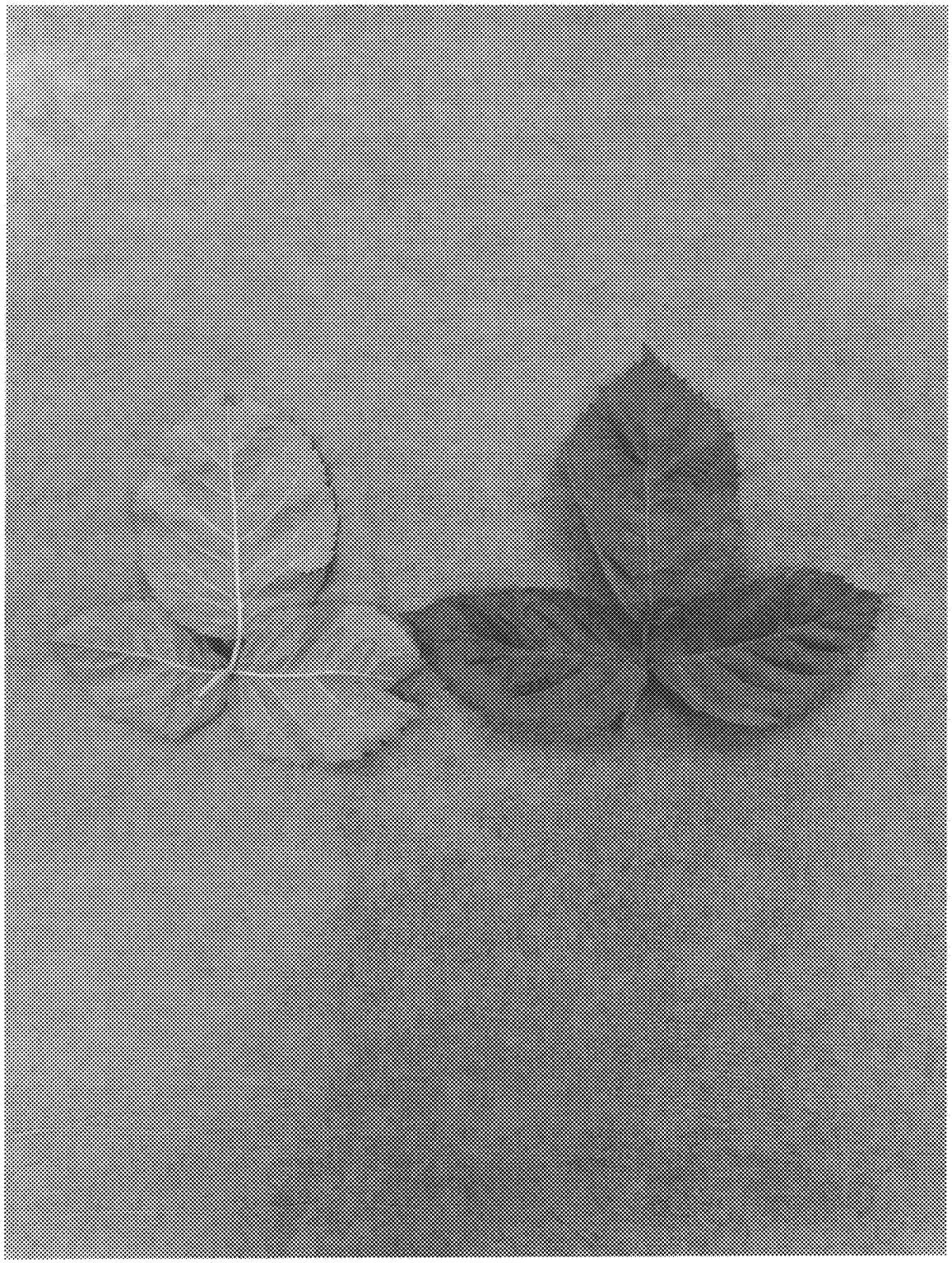
FIG. 3 illustrates the lower surface (left) and the upper surface (right) of leaves of variety 'DrisBlackTwentySix'.
Figure 4:
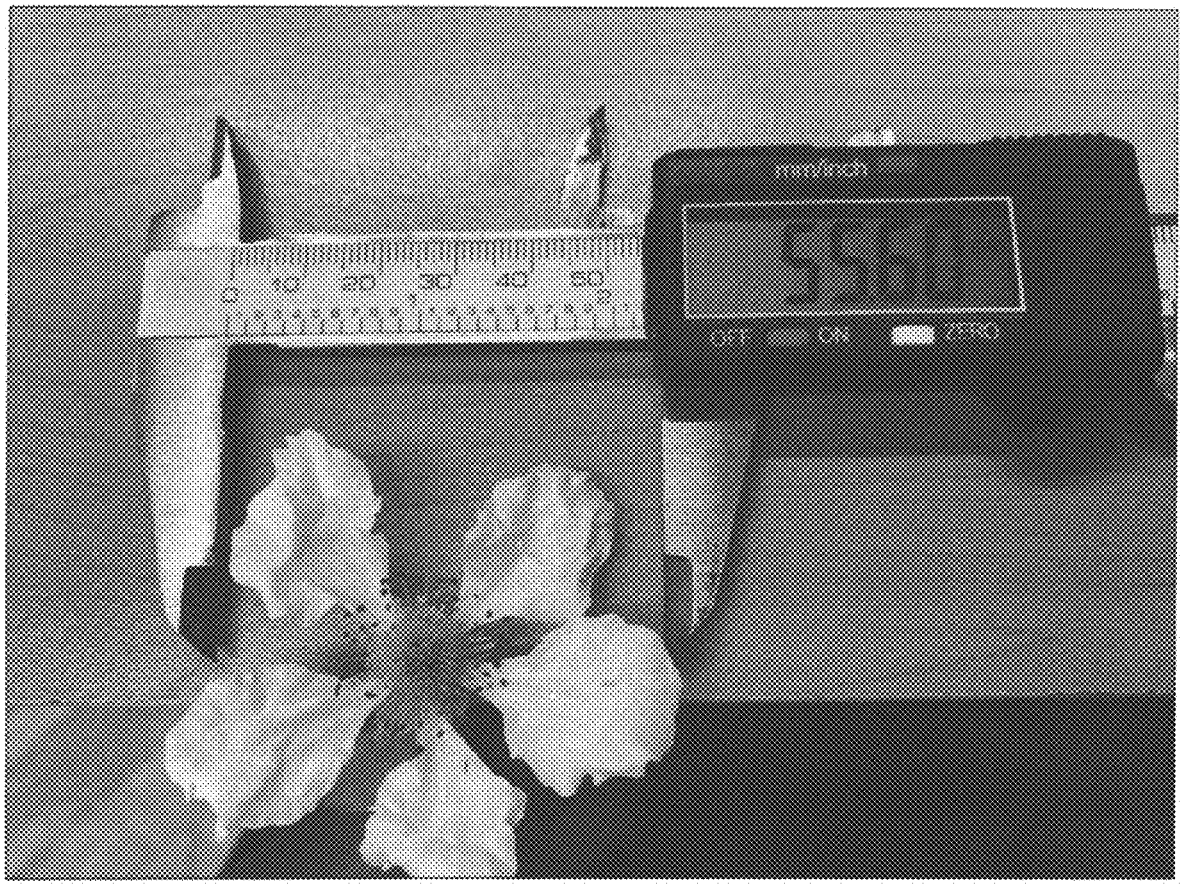
FIG. 4 illustrates an upper surface view of a mature flower of variety 'DrisBlackTwentySix'.

The following descriptions set forth the distinctive characteristics of 'DrisBlackTwentySix'. The data that define these characteristics are based on observations taken in Ciudad Guzmán, Mexico from 2015 to 2021. This description is in accordance with UPOV terminology. Color designations, color descriptions, and other phenotypical descriptions may deviate from the stated values and descriptions depending upon variation in environmental, seasonal, climatic and cultural conditions. 'DrisBlackTwentySix' has not been observed under all possible environmental conditions. The botanical description of 'DrisBlackTwentySix' was taken from plants that were three years old. The indicated values represent averages calculated. from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family.*—Rosaceae.

*Botanical.*—*Rubus* L. subgenus *Rubus*.

*Common name.*—Blackberry.

*Plant variety name.*—'DrisBlackTwentySix'.

Parentage:

*Female parent.*—Proprietary blackberry plant 'BR382.2' (unpatented).

*Male parent.*—Proprietary blackberry plant 'BR502.2' (unpatented).

Plant:

*Propagation.*—Root cuttings and tissue culture.

*Growth habit.*—Upright to semi-upright.

*Height.*—188.1 cm.

*Width.*—75.4 cm.

*Height/width ratio.*—2.49.

*Vigor.*—Medium.

*Self-fruitfulness.*—Self-fruitful.

Canes:

*Internodal distance.*—3.305 cm.

*New cane.*—Strength: Very strong. Glaucosity (waxy bloom): Medium.

*Dormant cane.*—Anthocyanin coloration: Absent. Predominant distribution of branches: Over whole length. Cross-section: Angular. Spine: Presence of spines: Present. Length: 5.15 mm. Width: 1.871 mm. Color: RHS 144A (Strong yellow-green). Density of spines on central third of cane: Dense. Surface texture: Rough. Flexibility: Rigid. Attitude of spine apex in relation to cane: Downwards.

*Young shoots.*—Length: 69 cm. Diameter: 0.844 cm. Anthocyanin coloration (during rapid growth): Absent. Color of young shoot: RHS NN137B (Greyish olive green). Number of glandular hairs: Absent or few. Time of young shoot emergence: Mid-April.

*Fruiting lateral.*—Fruiting lateral length (4$^{th}$ lateral from tip): 33.81 cm. Number of fruits per fruiting lateral: 11.1.

Leaves:

*Time of leaf bud burst.*—Mid-March.

*Leaf.*—Predominant number of leaflets: During strong vegetative growth, the predominant number of leaflets is 5, whereas during leaf bud burst the predominant number of leaflets is 3. Type: Palmate. Relative position of lateral leaflets: Overlapping. Arrangement: Opposite. Venation: Reticulate. Vein color: RHS 1.46A (Moderate yellow-green). Color of upper side: RHS NN137A (Greyish olive green). Color of under side: RHS 146B (Moderate yellow-green). Profile in cross-section: Concave (margins rolled inwards). Glossiness of upper side: Medium.

*Leaflet.*—Type of incision of margin: Bi-serrate. Depth of incisions: Deep.

*Terminal leaflet* (*for both those leaves with three leaflets and those leaves with five leaflets*).—Length: 8.47 cm. Width: 6.24 cm. Length/width ratio: 1.357. Lobing: Absent. Shape in cross-section: U-shaped. Undulation of margin: Absent or very weak. Blistering between veins: Strong. Shape: Ovate. Apex: Acute. Base: Obtuse. Margin: Doubly serrate.

*Lateral leaflet* (*single leaflet in basal pair*)(*for both those leaves with three leaflets and those leaves with five leaflets*).—Length: 7.83 cm. Width: 5.14 cm. Length/width ratio: 1.523. Shape: Oval. Apex: Convex. Base: Obtuse. Margin: Serrate.

*Rachis* (*length between terminal leaflet and adjacent lateral leaflets*).—2.22 cm.

*Petiole.*—Length: 6.092 cm. Diameter: 2.701 mm. Color of upper surface: RHS 144A (Strong yellow-green). Color of under surface: RHS 144A (Strong yellow-green).

*Stipule.*—Length: 0.939 cm. Width: 1.725 mm. Color: RHS 146A (Moderate olive green). Orientation: Erect.

Inflorescence:

*Flower bud.*—Length: 9.046 mm. Width: 7.35 mm. Color: RHS 62D (Pale purplish pink).

*Flower.*—Diameter (mature flowers): 54.312 mm. Number of flowers observed at 3$^{rd}$ node from tip of lateral: 7.6. Fragrance: Very faint or absent.

*Petal.*—Length: 26.69 mm. Width: 17.17 mm. Length/width ratio: 1.55. Number of petals per flower: 9.1. Color of upper and lower side: RHS NN155D (White). Shape: Orbicular. Apex: Rounded. Base: Attenuate. Margin: Entire.

*Sepal.*—Length: 8.934 mm. Width: 5.53 mm. Color: RHS 146B (Moderate yellow-green). Number per flower: 5.

*Flower pedicel.*—Length: 53.72 mm. Diameter: 1.599 mm. Color: RHS 144A (Strong yellow-green).

*Inflorescence peduncle.*—Length: 47.104 mm. Diameter: 4.002 mm. Color: RHS 146C (Moderate yellow-green).

*Reproductive organs.*—Style: Length: 7.56 mm. Color: RHS 149D (Pale yellow-green). Ovary: Color: RHS 149C (Brilliant yellow green). Stamen: Length: 1.05 mm. Color: RHS 145C (Light yellow-green). Pollen: Color: RHS 146A (Moderate olive green).

*Time of beginning of flowering on previous year's cane* (*floricane*).—Mid-January to mid-February.

*Time of beginning of flowering on current year's cane* (*primocane*).—Mid-July to mid-August.

Fruit:

*Length of mature fruit.*—37.304 mm.

*Diameter of mature fruit.*—21.605 mm.

*Ratio of length to width.*—1.72.

*Primocane fruit weight.*—13.2 g/fruit.

*Floricane fruit weight.*—9.5 g/fruit.

*Sweetness/soluble solids* (*in °brix*).—13.01.

*Titratable acidity* (*% as citric acid*).—1.51%.

*Glossiness.*—Strong.

*Firmness.*—Very firm.

*Fruit shape in longitudinal section.*—Long conical.

*Fruit color.*—RHS 202A (Black).

*Drupelet* (*single drupe*).—Length of drupelet: 4.77 mm. Diameter of drupelet: 4.49 mm. Average number of drupelets per fruit: 106.9.

*Seed.*—Diameter: 1.79 mm. Weight: 0.011 g/seed. Color: RHS 165A (Moderate brown).

*Flavor.*—Sweet with low acidity.

*Fruiting on current year's cane* (*primocane*).—Present.

*Harvest interval on previous year's cane* (*floricane*).—Mid-March to mid-May.

*Harvest interval on current year's cane* (*primocane*) .—Early September to mid-December.

*Yield.*—17,750 kg to 29,450 kg of fruit per hectare per season from 12-month-old plants when grown in Ciudad Guzmán, Mexico.

*Market use of fruit.*—Fresh market.

*Shipping and storage characteristics.*—Following harvest, fruit can be stored for 7 days if maintained under cooled temperatures that are standard for blackberry storage.

Resistance to pests and diseases:

*Powdery mildew* (*Podosphaera macularis*).—Moderately resistant.

*Fusarium wilt* (*Fusarium oxysporum*).—Resistant.

COMPARISONS TO PARENTAL AND REFERENCE BLACKBERRY VARIETIES

'DrisBlackTwentySix' differs from the female parent 'BR382.2' (unpatented) in that 'DrisBlackTwentySix' has improved flavor and larger fruit size as compared to 'BR382.2'.

'DrisBlackTwentySix' differs from the male parent 'BR502.2' (unpatented) in that 'DrisBlackTwentySix' has improved flavor and larger fruit size when compared to 'BR502.2'.

'DrisBlackTwentySix' differs from the reference variety 'DrisBlackThirteen' (U.S. Plant Pat. No. 27,681) in that 'DrisBlackTwentySix' has absent anthocyanin coloration on dormant cane, spines are present on dormant cane, U-shaped cross-section of terminal leaflet, and long conical fruit shape in longitudinal section, whereas 'DrisBlackThirteen' has medium amount of anthocyanin coloration on dormant cane, spines are absent on dormant cane, V-shaped cross-section of terminal leaflet, and medium ovate fruit shape in longitudinal section.

'DrisBlackTwentySix' differs from the reference variety 'DrisBlackSeventeen' (U.S. Plant Pat. No. 31,291) in that 'DrisBlackTwentySix' has absent anthocyanin coloration on dormant cane, predominant distribution of branches over whole length of dormant cane, downwards attitude of spine apex in relation to cane, and long conical fruit shape in longitudinal section, whereas 'DrisBlackSeventeen' has weak anthocyanin coloration on dormant cane, predominant distribution of branches only on upper half of dormant cane, upwards attitude of spine apex in relation to cane, and medium ovate fruit shape in longitudinal section.

What is claimed is:

1. new and distinct variety of blackberry plant designated 'DrisBlackTwentySix' as shown and described herein.

* * * * *